(12) United States Patent
Koverech et al.

(10) Patent No.: US 9,125,903 B2
(45) Date of Patent: Sep. 8, 2015

(54) COMPOSITION USEFUL FOR THE TREATMENT OF LIPID METABOLISM DISORDERS

(75) Inventors: Aleardo Koverech, Rome (IT); Ashraf Virmani, Ariccia (IT)

(73) Assignee: SIGMA-TAU INDUSTRIE FARMACEUTICHE RIUNITE, S.P.A., Rome (IT)

( * ) Notice: Subject to any disclaimer, the term of this patent is extended or adjusted under 35 U.S.C. 154(b) by 83 days.

(21) Appl. No.: 14/114,830

(22) PCT Filed: Apr. 24, 2012

(86) PCT No.: PCT/EP2012/057428
§ 371 (c)(1),
(2), (4) Date: Dec. 6, 2013

(87) PCT Pub. No.: WO2012/150146
PCT Pub. Date: Nov. 8, 2012

(65) Prior Publication Data
US 2014/0086985 A1    Mar. 27, 2014

(30) Foreign Application Priority Data
May 3, 2011 (EP) .................... 11164526

(51) Int. Cl.
| | |
|---|---|
| *A61K 9/12* | (2006.01) |
| *A61K 9/127* | (2006.01) |
| *A61K 38/43* | (2006.01) |
| *A23L 1/30* | (2006.01) |
| *A23L 1/302* | (2006.01) |
| *A23L 1/305* | (2006.01) |
| *A61K 33/30* | (2006.01) |
| *A61K 45/06* | (2006.01) |
| *A61K 36/899* | (2006.01) |
| *A61K 31/045* | (2006.01) |
| *A61K 31/05* | (2006.01) |
| *A61K 31/197* | (2006.01) |
| *A61K 31/202* | (2006.01) |
| *A61K 31/4415* | (2006.01) |
| *A61K 31/714* | (2006.01) |
| *A61K 36/062* | (2006.01) |

(52) U.S. Cl.
CPC . *A61K 38/43* (2013.01); *A23L 1/30* (2013.01); *A23L 1/3002* (2013.01); *A23L 1/302* (2013.01); *A23L 1/3006* (2013.01); *A23L 1/3051* (2013.01); *A61K 31/045* (2013.01); *A61K 31/05* (2013.01); *A61K 31/197* (2013.01); *A61K 31/202* (2013.01); *A61K 31/4415* (2013.01); *A61K 31/714* (2013.01); *A61K 33/30* (2013.01); *A61K 36/899* (2013.01); *A61K 45/06* (2013.01); *A61K 36/062* (2013.01)

(58) Field of Classification Search
None
See application file for complete search history.

(56) References Cited

FOREIGN PATENT DOCUMENTS

EP    0780124    6/1997

OTHER PUBLICATIONS

David J. Becker, MD., et al., Simvastatin vs Therapeutic Lifestyle Changes . . . , Mayo Clin Proc., vol. 83, No. 7, pp. 758-764 2008.
Krista A. Varady, et al., Role of Policosanols in the Prevention and Treatment . . . , Nutrition Reviews, vol. 61, No. 11, pp. 376-383, 2003.
Han Dong Hao, et al., Mechanisms of Cardiovascular . . . , Journal of Medicinal Food, vol. 7, No. 3, pp. 290-298, 2004.
Salvatore Pepe, et al., Coenzyme Q10 in Cardiovascular Disease, Mitochondrion, vol. 7, pp. A154-S167, 2007.
International Search Report issued in counterpart PCT Application No. PCT/EP2012/057428, Oct. 30, 2013.
Written Opinion of International Searching Authority issued in counterpart PCT Application No. PCT/EP2012/057428, Oct. 30, 2013.

*Primary Examiner* — Snigdha Maewall
(74) *Attorney, Agent, or Firm* — Lucas & Mercanti, LLP

(57) ABSTRACT

The present invention relates to a composition useful for the treatment of lipid metabolism disorders, comprising one or more of the following active ingredients: (a) extract of rice fermented with *Monascus purpureus*, (b) at least one omega-3 fatty acid, (c) L-carnitine or a salt thereof; and one or more of the following active ingredients: (d) at least one policosanol or a natural extract containing policosanols; (e) resveratrol or a natural extract containing resveratrol; (f) Coenzyme Q10; and (g) at least one vitamin.

11 Claims, No Drawings

COMPOSITION USEFUL FOR THE TREATMENT OF LIPID METABOLISM DISORDERS

This application is a U.S. national stage of PCT/EP2012/057428 filed on Apr. 24, 2012, which claims priority to and the benefit of European Application No. 11164526.3, filed on May 3, 2011, the contents of each of which are incorporated herein by reference.

FIELD OF THE INVENTION

The present invention relates to a combination of active ingredients and to compositions containing this combination for the medical and nutritional use, in the preparation of medicines or food supplements useful for prophylaxis and/or treatment of lipid metabolism disorders and their complications.

In particular, the present invention relates to a composition comprising as active ingredients (a) extract of rice fermented with *Monascus purpureus*; (b) at least one omega-3 fatty acid; (c) L-carnitine or a salt thereof; and one or more of the following active ingredients: (d) at least one policosanol or a natural extract containing policosanols; (e) resveratrol or a natural extract containing resveratrol; (f) Coenzyme Q10; and (g) at least one vitamin.

BACKGROUND OF THE INVENTION

Cardiovascular diseases related to abnormal lipid metabolism are very frequent in industrialised countries. In Italy, for instance, they account for more than 40% of the overall mortality (Capocaccia R., Farchi G., Prati S. et al.: La mortalità in Italia nell'anno 1989. Rapporto ISTISAN 1992/22). Our knowledge of the relationships between cholesterol and coronary heart disease stem from epidemiological studies conducted over the past few years. The conclusions reached in these studies indicate that the development of severe coronary atherosclerosis and coronary heart disease are closely correlated with serum cholesterol levels (McGill H. C. Jr. et al.: The International Atherosclerosis Project. Lab. Invest. 18: 463-653, 1968; Keys A.: Seven Countries: Death and Coronary Heart Disease. Harvard University Press, Cambridge, 1980).

Correction of eating habits through suitable diet is invariably the first measure adopted in cases of hyperlipidaemia. Satisfactory results are not always achieved, however, owing to widespread intolerance of strict dietary discipline, to the severity of the hypercholesterolaemia, or to genetic-type resistance.

To achieve the desired results in these patients, i.e. normalisation of blood levels of triglycerides and cholesterol, pharmacological treatment has to be resorted to. Hypolipaemic drugs fall into two categories: those which above all reduce cholesterol and those which mainly reduce triglycerides.

The former group of drugs includes the statins, probucol and resins, while the latter group includes the fibrates, nicotinic acid and fatty acids belonging to the omega-3 series.

The statins (lovastatin, simvastatin, provastatin, fluvastatin, and the like) are inhibitors of hydroxy-methyl-glutaryl-coenzyme A (HMG-CoA) reductase. By inhibiting this enzyme, they reduce the hepatic synthesis of cholesterol (Lancet 1994; 334: 1383-1389). To compensate for the reduction of intracellular cholesterol the liver cell produces several receptors for LDL and VLDL lipoproteins, which are thus removed from the bloodstream.

The statins are drugs which are better tolerated than the other anticholesterolaemic agents, but are not without drawbacks, the side effects most commonly induced by these drugs being gastrointestinal disorders, skin rashes and headache.

It has been reported that though the statins lead to a reduction in the number of deaths due to coronary heart disease, an increase has been observed, in treated patients, of deaths caused by other events such as tumours or trauma (Davey-Smith G., Song F., Sheldon T. A.: Cholesterol lowering and mortality: the importance of considering initial level at risk. BMJ, 1993; 306: 1367-1373; Ravnshov U.: Cholesterol lowering trials in coronary heart disease: frequency of citation and outcome. BMJ 1992; 305: 15-19). The results of experiments in animals and human subjects have suggested that, to reduce cholesterol levels, pharmacological treatment with statins should be given only to patients at high risk for coronary disease in the short term (JAMA, 1996; 275: 55-60).

Red yeast rice is the product of yeast (*Monascus purpureus*) grown on rice, and is served as a dietary staple in some Asian countries. It contains several compounds collectively known as monacolins, substances known to inhibit cholesterol synthesis. One of these, "monacolin K," is a potent inhibitor of HMG-CoA reductase.

In American Journal of Clinical Nutrition, Vol. 69, No. 2, 231-236, February 1999 it is described the cholesterol-lowering effects of red-yeast-rice supplementation.

The omega-3 fatty acids are known for their triglyceride-lowering effects and for their effects in raising the levels of high-density lipoproteins (HDL).

In BMJ. 2006 April 1; 332(7544): 752-760 it is described the use of omega 3 fatty acids for treating cardiovascular diseases.

The policosanols are long-chain aliphatic alcohols. Examples of policosanols are triacontanol, hexacosanol, hexacontanol, ecocontanol, tetracosanol, dotriacontanol, and tetracontanol. The policosonol can be present as such or in the form of extract from natural products that contain it, e.g. wheat or rice germs, the waxy cuticle of sugar cane, or *Ginkgo biloba* leaves. Policosanols are widely used in the medical and nutritional field.

In Nutr Rev. 2003 November; 61(11):376-83 it is described the use of policosonol for treating cardiovascular diseases.

Resveratrol (trans-3,4',5-trihydroxystilbene) is a polyphenol molecule found in many plant species including grapes and others.

In Free Radic Res. 2000 July; 33(1):105-14 it is described the use of Resveratrol for the inhibition of lipid peroxidation.

Coenzyme Q10 is now so well known in its human use that it requires no particular explanation and the substance is available on the market. Experts in the sector can refer to the patent documents filed by the present applicant, where this substance is amply described.

Vitamin $B_6$ is a water-soluble vitamin and is part of the vitamin B complex group widely used in the medical and nutritional field. Several forms of the vitamin are known, but pyridoxal phosphate (PLP) is the active form and is a cofactor in many reactions of amino acid metabolism, including transamination, deamination, and decarboxylation. PLP also is necessary for the enzymatic reaction governing the release of glucose from glycogen.

Vitamin $B_{12}$, also called cobalamin, is a water soluble vitamin with a key role in the normal functioning of the brain and nervous system, and for the formation of blood. It is one of the eight B vitamins. It is normally involved in the metabolism of every cell of the human body, especially affecting DNA synthesis and regulation, but also fatty acid synthesis and energy production. As the largest and most structurally complicated vitamin, it can be produced industrially only through bacterial fermentation-synthesis.

Also Vitamin $B_{12}$ is widely used in the medical and nutritional field.

L-carnitine is a quaternary ammonium compound biosynthesized from the amino acids lysine and methionine. In living cells, it is required for the transport of fatty acids from the cytosol into the mitochondria during the breakdown of lipids (fats) for the generation of metabolic energy.

In U.S. Pat. No. 4,255,449 it is reported that L-carnitine is useful for increasing the HDL cholesterol and for treating diseases liked to high cholesterol level.

In WO040916029 it is reported that L-carnitine is useful the treatment of cardiovascular diseases.

While there are other publications available in which is shown that the compounds of the invention are useful for prophylaxis and/or treatment of hypertriglyceridemia and hypercholesterolemia and related disease states, none of them mention nor suggest about the unexpected synergistic effect shown by the composition of the invention.

SUMMARY OF THE INVENTION

It has now been found, unexpectedly, that the co-ordinated use, this term being defined precisely here below, of a composition comprising as active ingredients (a) extract of rice fermented with *Monascus purpureus*; (b) at least one omega-3 fatty acid; (c) L-carnitine or a salt thereof; and one or more of the following active ingredients: (d) at least one policosanol or a natural extract containing policosanols; (e) resveratrol or a natural extract containing resveratrol; (f) Coenzyme Q10; and (g) at least one vitamin; enables an enhanced effect on the anticholesterolaemic and antitriglyceridaemic action to be achieved as compared to the separate, independent administration of the active ingredients or their minimal combination.

It is therefore one object of the present invention a synergistic combination composition, comprising as active ingredients: (a) extract of rice fermented with *Monascus purpureus*; (b) at least one omega-3 fatty acid; (c) L-carnitine or a salt thereof; and one or more of the following active ingredients: (d) at least one policosanol or a natural extract containing policosanols; (e) resveratrol or a natural extract containing resveratrol; (f) Coenzyme Q10; and (g) at least one vitamin.

It is a further object of the present invention a synergistic composition comprising as active ingredients: (a) extract of rice fermented with *Monascus purpureus*; (b) at least one omega-3 fatty acid; (c) L-carnitine or a salt thereof; (d) at least one policosanol or a natural extract containing policosanols; (e) resveratrol or a natural extract containing resveratrol; (f) Coenzyme Q10; and optionally (g) at least one vitamin.

It is a further object of the present invention a synergistic composition comprising as active ingredients: (a) extract of rice fermented with *Monascus purpureus* in a dose of from 1 mg to 3000 mg, preferred doses is of from 10 mg to 2000 mg, the most preferred dose is 200 mg; (b) at least one omega-3 fatty acid in a dose of from 1 mg to 2000 mg, preferred doses is of from 10 mg to 1000 mg, the most preferred dose is 600 mg; (c) L-carnitine or a salt thereof in a dose of from 1 mg to 3000 mg, preferred doses is of from 10 mg to 1000 mg, the most preferred dose is 100 mg as inner salt; (d) at least one policosanol or a natural extract containing policosanols in a dose of from 0.1 mg to 1000 mg, preferred doses is of from 1 mg to 100 mg, the most preferred dose is 10 mg; (e) resveratrol or a natural extract containing resveratrol in a dose of from 0.1 mg to 1000 mg, preferred doses is of from 1 mg to 100 mg, the most preferred dose is 10 mg; (f) Coenzyme Q10 in a dose of from 0.1 mg to 1000 mg, preferred doses is of from 1 mg to 100 mg, the most preferred dose is 10 mg; (g) vitamin B6 in a dose of from 0.03 mg to 300 mg, preferred doses is of from 0.3 mg to 30 mg, the most preferred dose is 3 mg; and (h) vitamin B12 in a dose of from 0.025 mcg to 250 mcg, preferred doses is of from 0.25 mcg to 25 mcg, the most preferred dose is 2.5 µg (mcg).

It is a further object of the present invention a synergistic composition comprising as active ingredients: (a) extract of rice fermented with *Monascus purpureus* in a dose of 200 mg comprising 3 mg of Monacolin K; (b) fish oil in a dose of 600 mg comprising 120 mg of DHA and 165 mg of EPA; (c) L-carnitine tartrate in a dose of 147 mg corresponding to 100 mg of L-carnitine inner salt; (d) extract of sugar cane comprising policosanols in a dose of 10 mg; (e) resveratrol in a dose of 10 mg; (f) Coenzyme Q10 in a dose of 10 mg; (g) vitamin B6 in a dose of 3 mg; and (h) vitamin B12 in a dose of 2.5 mcg;

It is a further object of the present invention the compositions mentioned above, for use as anticholesterolaemic and antitriglyceridaemic agents, and for increasing HDL cholesterol.

It is a further object of the present invention the compositions mentioned above, for use for the prevention or treatment of altered lipid metabolism and complications thereof, in which said complications are selected from the group consisting of cardiovascular, atherosclerotic and/or thromboembolic diseases.

It is a further object of the present invention the compositions mentioned above, for preparing a medicament for the prevention or treatment of altered lipid metabolism and complications thereof, in which said complications are selected from the group consisting of cardiovascular, atherosclerotic and/or thromboembolic diseases.

It is a further object of the present invention the compositions mentioned above, for preparing a dietary supplement for the prevention or treatment of altered lipid metabolism and complications thereof, in which said complications are selected from the group consisting of cardiovascular, atherosclerotic and/or thromboembolic diseases.

It is a further object of the present invention a method for increasing HDL cholesterol and for decreasing cholesterol and triglycerides, which comprises administering to a patient in need thereof a suitable amount of a composition described above.

It is a further object of the present invention a method of preventing or treating an altered lipid metabolism and complications thereof, in which said complications are selected from the group consisting of cardiovascular, atherosclerotic and/or thromboembolic diseases, which comprises administering to a patient in need thereof a suitable amount of a composition described above.

The compositions of the invention may further comprise other vitamins, co-enzymes, mineral substances and antioxidants; or further active ingredients useful for treating lipid dismetabolism.

What is meant by salt of L-carnitine is any salt of the latter with an acid that does not give rise to toxic or side effects.

Non-limiting examples of such salts are: chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

A list of FDA-approved pharmaceutically acceptable salts is given in the publication Int. J. of Pharm. 33 (1986), 201-217.

DETAILED DESCRIPTION OF THE INVENTION

The *Monascus purpureus* used according to the invention is extract of red rice (*Oryza sativa*) fermented with red yeast (*Monascus purpureus*) having a title of 1.5% in monacolin K.

The omega-3 fatty acid according to the present invention can possibly be esterified or salified, These fatty acids can be obtained by synthesis or, preferably, from fish oil. In that case, it is possible to use various mixtures of omega-3 fatty acids depending on their characteristics. Preferably, the omega-3 fatty acids are the long-chain ones (from 20 to 22 carbon atoms). The ones most preferred are 5,8,11,14,17-eicosapentanoic acid (EPA) and cis 0,13,16,19-docosahexanoic acid (DHA). These omega-3 fatty acids can possibly be esterified or salified to pharmaceutically acceptable derivatives, with alcohols or bases, respectively. The omega-3 fatty acids, or their esters or salts, alone or in mixtures thereof, can be procured on the market, or can be prepared by known methods. The mixtures can be specifically formulated for the combination according to the invention)

The policosanols according to the present invention are long-chain aliphatic alcohols. Examples of policosanols are triacontanol, hexacosanol, hexacontanol, ecocontanol, tetracosanol, dotriacontanol, and tetracontanol. The policosonal can be present as such or in the form of extract from natural products that contain it, e.g. wheat or rice germs, the waxy cuticle of sugar cane, or *Ginkgo biloba* leaves.

Resveratrol according to the present invention is a polyphenol molecule found in many plant species including grapes and others. Polyphenols, including flavonoids, flavonols, catechins, and stilbenes are present in the human diet in plant materials, where they act as antioxidants and protect the plant from damage by bacteria, fungi, and ultraviolet radiation. Since resveratrol is present in wine, it has been postulated that it might be the reason for the "French Paradox," the epidemiological phenomenon in which the French population has a significantly lower incidence of cardiovascular disease, even though the French consume a diet higher in fat than other populations.

*Monascus purpureus*, omega-3 fatty acid, policosanol, resveratrol, Coenzyme Q10, Vitamin B6, Vitamin B12 and L-carnitine according to the present invention can be administrated in a "co-ordinated manner". What is meant by "co-ordinated manner" of the aforesaid compounds is, indifferently, either the co-administration, i.e. the substantially concomitant or sequential supplementation of *Monascus purpureus* and at least one of omega-3 fatty acid, at least one policosanol, resveratrol, Coenzyme Q10, Vitamin B6, Vitamin B12 and L-carnitine or the administration of a composition comprising the aforesaid active ingredients in combination and in a mixture optionally further comprising one or more excipients or diluents pharmaceutically acceptable.

The composition of the present invention is administered orally, in any suitable form. An example of form of administration is in a liquid, semi-liquid or solid form in sachets, pills, vials, ointment, gel or liposome.

*Monascus purpureus*, omega-3 fatty acids, policosanols, resveratrol, Coenzyme Q10, Vitamin B6, Vitamin B12 and L-carnitine according to the present invention are known compounds easily available on the market.

The composition according to the present invention is composed of active ingredients which are familiar to operators in the medical field and already in use. Said active ingredients are not endowed with the side effects of the antilipemic drugs known in the art (statins, probucol, resins and fibrates).

Their procurement therefore is very easy, inasmuch as these are products which have been on the market now for a long time and are of a grade suitable for human administration.

For any compound, the therapeutically effective dose can be estimated initially either in cell culture assays or in animal models, usually mice or rats.

The animal model may also be used to determine the appropriate concentration range and route of administration. Such information can then be used to determine useful doses and routes for administration in humans.

The precise effective dose for a human subject will depend upon the severity of the disease state, general health of the subject, age, weight, and gender of the subject, diet, time and frequency of administration, drug combination(s), reaction sensitivities, and tolerance/response to therapy.

This implies that, apart from the consideration of the synergistic effect demonstrated here below, the dosages and ratios of the individual components can be determined by the expert in the sector with normal preclinical and clinical trials, or with the usual considerations regarding the formulation of a dietetic product.

The compositions covered by the present invention are entirely conventional and are obtained with methods that are common practice in the pharmaceutical industry. The compositions according to the present invention contain, along with the active ingredient, at least one pharmaceutically acceptable vehicle or excipient. Particularly useful may be formulation adjuvants such as, for example, solubilising agents, dispersing agents, suspension agents and emulsifying agents. A general reference work is *Remington's Pharmaceutical Sciences Handbook*, latest edition.

The following non-limiting examples further illustrates the invention.

EXAMPLE 1

Serum Lipid-Lowering Activity in db/db Mice

Male CD 1 mice on a high-cholesterol diet (DP/104, Altromin-Rieper) for about 25 days were used. An acclimatization period of seven days was allowed before the start of the high-cholesterol diet.

Mice were housed inside cages with stainless steel cover-feed and sterilized and dust-free bedding cobs. Animals were housed under a light-dark cycle, keeping temperature and humidity constant. Parameters of the animal rooms are assessed as follows: $22\pm2°$ C. temperature, $55\pm10\%$ relative humidity, about 15-20 filtered air changes/hour and 12 hours circadian cycle of artificial light (7 a.m., 7 p.m.). The environmental conditions were monitored.

Mice were divided into groups (10 mice per group) and treated orally (1 mL) twice daily with the compounds of the invention or their combinations at the doses reported in the following:
  monacolin K 2 mg/kg (dissolved in water);
  fish oil 200 mg/kg (dissolved in ethanol);
  Hexacosanol 25 mg/kg (dissolved in ethanol);
  resveratrol 5 mg/kg (dissolved in ethanol);
  Coenzyme Q10 50 mg/kg (dissolved in water);
  Vitamin B6 0.3 mg/kg (dissolved in water);
  Vitamin B12 0.25 mg/kg (dissolved in water);

L-carnitine 20 mg/kg (dissolved in water).

At the start of treatment, the body weight of the animals was checked and monitoring of the animals' consumption of water and feed was scheduled.

On day 18, plasma cholesterol, triglyceride and HDL cholesterol were evaluated.

Blood samples were taken from the caudal vein with the aid of a Jelco 22G catheter (Johnson and Johnson) in post-absorption conditions (fasting from 9 a.m. to 4.30 p.m.) and 7.30 hours after the last treatment.

The results obtained are reported in the following Tables 1-3.

TABLE 1

Plasma total cholesterol levels in male CD1 mice (ten mice for each group) on high-cholesterol diet orally treated with the compounds of the invention or their combinations, or vehicle, twice a day for 17 days and one time on day 18. Blood collection in post-absorptive state (fasting: 9:00 a.m.-5:00 p.m.), at 8 h from last treatment. Mean values ± S.E. Student's t-test.

| Group | Treatment | Total-cholesterol (mg/dL) Mean values ± S.E. | % Reduction | Student's t-test P< | VS |
|---|---|---|---|---|---|
| 1 | Control (high-cholesterol diet) | 366.8 ± 17.3 | — | — | — |
| 2 | Standard diet (vehicle) | 143.4 ± 16.1 | −60 | 0.001 | Cont. |
| 3 | Monacolin K 2 mg/kg | 289.7 ± 21.0 | −21 | 0.05 | Cont. |
| 4 | Fish oil 200 mg/kg | 337.4 ± 23.4 | −8 | NS | Cont. |
| 5 | Hexacosanol 25 mg/kg | 307.2 ± 23.9 | −16 | NS | Cont. |
| 6 | Resveratrol 5 mg/kg | 352.1 ± 19.1 | −4 | NS | Cont. |
| 7 | Coenzyme Q10 50 mg/kg | 355.8 ± 25.2 | −3 | NS | Cont. |
| 8 | Vitamin B6 0.3 mg/kg | 348.5 ± 18.5 | −5 | NS | Cont. |
| 9 | Vitamin B12 0.25 mg/kg | 352.1 ± 20.2 | −4 | NS | Cont. |
| 10 | L-carnitine 20 mg/kg | 322.8 ± 21.1 | −12 | NS | Cont. |
| 11 | Monacolin K Fish oil | 278.7 ± 26.7 | −24 | 0.05 | Cont. |
| 12 | Monacolin K Hexacosanol | 264.1 ± 22.3 | −28 | 0.01 | Cont. |
| 13 | Monacolin K Resveratrol | 282.4 ± 24.6 | −23 | 0.05 | Cont. |
| 14 | Monacolin K L-carnitine | 286.1 ± 23.1 | −22 | 0.05 | Cont. |
| 15 | Monacolin K Fish oil Hexacosanol | 263.1 ± 24.7 | −28 | 0.01 | Cont. |
| 16 | Monacolin K Fish oil Resveratrol | 278.7 ± 25.8 | −24 | 0.05 | Cont. |
| 17 | Monacolin K Fish oil L-carnitine | 275.3 ± 27.6 | −25 | 0.05 | Cont. |
| 18 | Fish oil Hexacosanol Resveratrol | 278.8 ± 26.9 | −24 | 0.05 | Cont. |
| 19 | Fish oil Hexacosanol L-carnitine | 275.0 ± 26.7 | −25 | 0.01 | Cont. |
| 20 | Fish oil Resveratrol L-carnitine | 333.7 ± 24.8 | −9 | NS | Cont. |
| 21 | Monacolin K Fish oil | 253.4 ± 24.3 | −31 | 0.01 | Cont. |
| 22 | Hexacosanol Resveratrol Monacolin K Fish oil | 256.7 ± 24.8 | −30 | 0.01 | Cont. |
| 23 | Hexacosanol L-carnitine Monacolin K Fish oil | 268.7 ± 26.6 | −24 | 0.05 | Cont. |
| 24 | Resveratrol L-carnitine Fish oil Hexacosanol Resveratrol L-carnitine | 282.0 ± 26.0 | −23 | 0.05 | Cont. |
| 25 | Monacolin K Hexacosanol Resveratrol L-carnitine | 256.8 ± 27.1 | −30 | 0.01 | Cont. |
| 26 | Monacolin K Fish oil Hexacosanol Resveratrol Vitamin B6 Vitamin B12 L-carnitine | 176.0 ± 33.6 | −52 | 0.001 | Cont. |
| 27 | Monacolin K Fish oil Hexacosanol Vitamin B6 Vitamin B12 L-carnitine | 190.7 ± 30.3 | −48 | 0.001 | Cont. |
| 28 | Fish oil Hexacosanol Resveratrol Vitamin B6 Vitamin B12 L-carnitine | 242.1 ± 31.1 | −34 | 0.01 | Cont. |
| 29 | Monacolin K Hexacosanol Resveratrol Vitamin B6 Vitamin B12 L-carnitine | 276.1 ± 26.6 | −25 | 0.01 | Cont. |
| 30 | Monacolin K Fish oil Resveratrol- Vitamin B6 Vitamin B12 L-carnitine | 220.0 ± 28.6 | −40 | 0.001 | Cont. |
| 31 | Monacolin K Fish oil Hexacosanol Resveratrol Coenzyme Q10 L-carnitine | 183.4 ± 29.5 | −50 −30 −34 −33 −34 −33 −45 | 0.001 0.05 0.05 0.05 0.05 0.05 0.05 | Cont. 15 16 17 18 19 20 |
| 32 | Monacolin K Fish oil Hexacosanol Coenzyme Q10 L-carnitine | 220.3 ± 29.4 | −40 | 0.001 | Cont. |
| 33 | Fish oil Hexacosanol Resveratrol Coenzyme Q10 | 242.0 ± 33.7 | −34 | 0.01 | Cont. |

TABLE 1-continued

Plasma total cholesterol levels in male CD1 mice (ten mice for each group) on high-cholesterol diet orally treated with the compounds of the invention or their combinations, or vehicle, twice a day for 17 days and one time on day 18. Blood collection in post-absorptive state (fasting: 9:00 a.m.-5:00 p.m.), at 8 h from last treatment.
Mean values ± S.E.
Student's t-test.

| Group | Treatment | Total-cholesterol (mg/dL) Mean values ± S.E. | % Reduction | Student's t-test P< | VS |
|---|---|---|---|---|---|
| 34 | L-carnitine Monacolin K Hexacosanol Resveratrol Coenzyme Q10 | 223.7 ± 34.5 | −39 | 0.001 | Cont. |
| 35 | L-carnitine Monacolin K Fish oil Resveratrol Coenzyme Q10 | 234.7 ± 35.7 | −36 | 0.01 | Cont. |
| 36 | L-carnitine Monacolin K Fish oil Hexacosanol Resveratrol Coenzyme Q10 Vitamin B6 Vitamin B12 L-carnitine | 94.3 ± 6.2 | −74 −63 −63 −63 −63 −46 −51 −61 −48 | 0.001 0.001 0.001 0.001 0.001 0.05 0.01 0.001 0.05 | Cont. 15 21 22 25 26 27 28 31 |

TABLE 2

Plasma triglycerides levels in male CD1 mice (ten mice for each group) on high-cholesterol diet orally treated with the compounds of the invention or their combinations, or vehicle, twice a day for 17 days and one time on day 18. Blood collection in post-absorptive state (fasting: 9:00 a.m.-5:00 p.m.), at 8 h from last treatment.
Mean values ± S.E.
Student's t-test.

| Group | Treatment | Triglycerides (mg/dL) Mean values ± S.E. | % Reduction | Student's t-test P< | VS |
|---|---|---|---|---|---|
| 1 | Control (high-cholesterol diet) | 202.5 ± 19.7 | — | — | — |
| 2 | Standard diet (vehicle) | 35.5 ± 6.3 | −82 | 0.001 | Cont. |
| 3 | Monacolin K 2 mg/kg | 186.3 ± 20.8 | −8 | NS | Cont. |
| 4 | Fish oil 200 mg/kg | 182.2 ± 20.7 | −10 | NS | Cont. |
| 5 | Hexacosanol 25 mg/kg | 172.1 ± 12.3 | −15 | NS | Cont. |
| 6 | Resveratrol 5 mg/kg | 157.9 ± 12.4 | −22 | 0.05 | Cont. |
| 7 | Coenzyme Q10 50 mg/kg | 196.4 ± 22.1 | −3 | NS | Cont. |
| 8 | Vitamin B6 0.3 mg/kg | 194.3 ± 16.7 | −4 | NS | Cont. |
| 9 | Vitamin B12 0.25 mg/kg | 194.5 ± 17.4 | −4 | NS | Cont. |
| 10 | L-carnitine 20 mg/kg | 192.5 ± 16.4 | −5 | NS | Cont. |
| 11 | Monacolin K Fish oil | 172.3 ± 15.4 | −15 | NS | Cont. |
| 12 | Monacolin K Hexacosanol | 158.0 ± 12.5 | −22 | 0.05 | Cont. |
| 13 | Monacolin K Resveratrol | 143.8 ± 11.2 | −29 | 0.01 | Cont. |
| 14 | Monacolin K L-carnitine | 178.3 ± 13.4 | −12 | NS | Cont. |
| 15 | Monacolin K Fish oil Hexacosanol | 135.7 ± 13.9 | −33 | 0.01 | Cont. |
| 16 | Monacolin K Fish oil Resveratrol | 135.1 ± 14.2 | −33 | 0.01 | Cont. |
| 17 | Monacolin K Fish oil L-carnitine | 149.9 ± 12.1 | −26 | 0.05 | Cont. |
| 18 | Fish oil Hexacosanol Resveratrol | 131.6 ± 11.7 | −35 | 0.01 | Cont. |
| 19 | Fish oil Hexacosanol L-carnitine | 141.8 ± 16.7 | −30 | 0.01 | Cont. |
| 20 | Fish oil Resveratrol L-carnitine | 135.6 ± 13.3 | −33 | 0.01 | Cont. |
| 21 | Monacolin K Fish oil Hexacosanol Resveratrol | 146.8 ± 15.9 | −27 | 0.01 | Cont. |
| 22 | Monacolin K Fish oil Hexacosanol L-carnitine | 137.8 ± 14.4 | −32 | 0.01 | Cont. |
| 23 | Monacolin K Fish oil Resveratrol L-carnitine | 125.6 ± 11.6 | −38 | 0.01 | Cont. |
| 24 | Fish oil Hexacosanol Resveratrol L-carnitine | 131.6 ± 14.5 | −35 | 0.01 | Cont. |
| 25 | Monacolin K Hexacosanol Resveratrol L-carnitine | 137.7 ± 14.8 | −32 | 0.01 | Cont. |
| 26 | Monacolin K Fish oil Hexacosanol Resveratrol Vitamin B6 Vitamin B12 L-carnitine | 83.0 ± 15.0 | −59 | 0.001 | Cont. |
| 27 | Monacolin K Fish oil Hexacosanol Vitamin B6 Vitamin B12 L-carnitine | 81.0 ± 17.1 | −60 | 0.001 | Cont. |
| 28 | Fish oil Hexacosanol Resveratrol Vitamin B6 Vitamin B12 L-carnitine | 117.5 ± 13.6 | −42 | 0.001 | Cont. |
| 29 | Monacolin K Hexacosanol Resveratrol Vitamin B6 Vitamin B12 L-carnitine | 121.5 ± 12.0 | −40 | 0.001 | Cont. |

TABLE 2-continued

Plasma triglycerides levels in male CD1 mice (ten mice for each group) on high-cholesterol diet orally treated with the compounds of the invention or their combinations, or vehicle, twice a day for 17 days and one time on day 18. Blood collection in post-absorptive state (fasting: 9:00 a.m.-5:00 p.m.), at 8 h from last treatment. Mean values ± S.E. Student's t-test.

| Group | Treatment | Triglycerides (mg/dL) Mean values ± S.E. | % Reduction | Student's t-test P< | VS |
|---|---|---|---|---|---|
| 30 | L-carnitine Monacolin K Fish oil Resveratrol-Vitamin B6 Vitamin B12 | 107.3 ± 13.2 | −47 | 0.001 | Cont. |
| 31 | L-carnitine Monacolin K Fish oil Hexacosanol Resveratrol Coenzyme Q10 L-carnitine | 85.3 ± 19.2 | −58 −37 −37 −43 −35 −40 −37 | 0.001 0.05 0.05 0.01 0.05 0.05 0.05 | Cont. 15 16 17 18 19 20 |
| 32 | Monacolin K Fish oil Hexacosanol Coenzyme Q10 L-carnitine | 81.0 ± 21.1 | −60 | 0.001 | Cont. |
| 33 | Fish oil Hexacosanol Resveratrol Coenzyme Q10 L-carnitine | 91.1 ± 23.0 | −55 | 0.001 | Cont. |
| 34 | Monacolin K Hexacosanol Resveratrol Coenzyme Q10 L-carnitine | 113.4 ± 15.3 | −44 | 0.001 | Cont. |
| 35 | Monacolin K Fish oil Resveratrol Coenzyme Q10 L-carnitine | 111.4 ± 15.7 | −45 | 0.001 | Cont. |
| 36 | Monacolin K Fish oil Hexacosanol Resveratrol Coenzyme Q10 Vitamin B6 Vitamin B12 L-carnitine | 15.2 ± 10.2 | −92 −89 −89 −89 −89 −82 −81 −87 −82 | 0.001 0.001 0.001 0.001 0.001 0.01 0.01 0.001 0.01 | Cont. 15 21 22 25 26 27 28 31 |

TABLE 3

Plasma HDL-cholesterol levels in male CD1 mice (ten mice for each group) on high-cholesterol diet orally treated with the compounds of the invention or their combinations, or vehicle, twice a day for 17 days and one time on day 18. Blood collection in post-absorptive state (fasting: 9:00 a.m.-5:00 p.m.), at 8 h from last treatment. Mean values ± S.E. Student's t-test.

| Group | Treatment | HDL-cholesterol (mg/dL) | % of increase | Student's t-test P< | VS |
|---|---|---|---|---|---|
| 1 | Control (high-cholesterol diet) | 23.0 ± 2.3 | — | — | — |
| 2 | Standard diet | 30.6 ± 2.4 | +33 | 0.05 | Cont. |
| 3 | (vehicle) Monacolin K 2 mg/kg | 25.3 ± 2.1 | +10 | NS | Cont. |
| 4 | Fish oil 200 mg/kg | 27.6 ± 1.8 | +20 | NS | Cont. |
| 5 | Hexacosanol 25 mg/kg | 26.4 ± 2.0 | +15 | NS | Cont. |
| 6 | Resveratrol 5 mg/kg | 23.7 ± 1.9 | +3 | NS | Cont. |
| 7 | Coenzyme Q10 50 mg/kg | 23.9 ± 2.2 | +4 | NS | Cont. |
| 8 | Vitamin B6 0.3 mg/kg | 24.1 ± 2.5 | +5 | NS | Cont. |
| 9 | Vitamin B12 0.25 mg/kg | 24.3 ± 23 | +5 | NS | Cont. |
| 10 | L-carnitine 20 mg/kg | 27.8 ± 2.1 | +21 | NS | Cont. |
| 11 | Monacolin K Fish oil | 29.2 ± 2.6 | +27 | NS | Cont. |
| 12 | Monacolin K Hexacosanol | 28.3 ± 2.4 | +23 | NS | Cont. |
| 13 | Monacolin K Resveratrol | 25.8 ± 2.1 | +12 | NS | Cont. |
| 14 | Monacolin K L-carnitine | 29.4 ± 2.5 | +27 | NS | Cont. |
| 15 | Monacolin K Fish oil Hexacosanol | 30.6 ± 2.6 | +33 | 0.05 | Cont. |
| 16 | Monacolin K Fish oil Resveratrol | 30.8 ± 2.8 | +34 | 0.05 | Cont. |
| 17 | Monacolin K Fish oil L-carnitine | 34.5 ± 3.2 | +50 | 0.01 | Cont. |
| 18 | Fish oil Hexacosanol Resveratrol | 30.6 ± 2.7 | +33 | 0.05 | Cont. |
| 19 | Fish oil Hexacosanol L-carnitine | 32.6 ± 3.2 | +42 | 0.05 | Cont. |
| 20 | Fish oil Resveratrol L-carnitine | 32.4 ± 3.4 | +41 | 0.05 | Cont. |
| 21 | Monacolin K Fish oil Hexacosanol Resveratrol | 32.9 ± 3.1 | +43 | 0.05 | Cont. |
| 22 | Monacolin K Fish oil Hexacosanol L-carnitine | 34.0 ± 2.9 | +47 | 0.01 | Cont. |
| 23 | Monacolin K Fish oil Resveratrol L-carnitine | 34.5 ± 3.3 | +50 | 0.01 | Cont. |
| 24 | Fish oil Hexacosanol Resveratrol L-carnitine | 34.7 ± 3.4 | +51 | 0.01 | Cont. |
| 25 | Monacolin K Hexacosanol Resveratrol L-carnitine | 33.4 ± 3.5 | +45 | 0.05 | Cont. |
| 26 | Monacolin K Fish oil Hexacosanol Resveratrol | 34.3 ± 3.2 | +49 | 0.05 | Cont. |

TABLE 3-continued

Plasma HDL-cholesterol levels in male CD1 mice (ten mice for each group) on high-cholesterol diet orally treated with the compounds of the invention or their combinations, or vehicle, twice a day for 17 days and one time on day 18. Blood collection in post-absorptive state (fasting: 9:00 a.m.-5:00 p.m.), at 8 h from last treatment. Mean values ± S.E. Student's t-test.

| Group | Treatment | HDL-cholesterol (mg/dL) | % of increase | Student's t-test P< | VS |
|---|---|---|---|---|---|
| 27 | Vitamin B6<br>Vitamin B12<br>L-carnitine<br>Monacolin K<br>Fish oil<br>Hexacosanol | 34.1 ± 3.0 | +48 | 0.01 | Cont. |
| 28 | Vitamin B6<br>Vitamin B12<br>L-carnitine<br>Fish oil<br>Hexacosanol<br>Resveratrol | 33.6 ± 3.2 | +46 | 0.01 | Cont. |
| 29 | Vitamin B6<br>Vitamin B12<br>L-carnitine<br>Monacolin K<br>Hexacosanol<br>Resveratrol | 33.8 ± 3.1 | +47 | 0.05 | Cont. |
| 30 | Vitamin B6<br>Vitamin B12<br>L-carnitine<br>Monacolin K<br>Fish oil<br>Resveratrol | 33.5 ± 3.3 | +45 | 0.05 | Cont. |
| 31 | Vitamin B6<br>Vitamin B12<br>L-carnitine<br>Monacolin K<br>Fish oil<br>Hexacosanol<br>Resveratrol<br>Coenzyme Q10 | 33.5 ± 3.2 | +45 | 0.05 | Cont. |
| 32 | L-carnitine<br>Monacolin K<br>Fish oil<br>Hexacosanol<br>Coenzyme Q10 | 35.4 ± 3.6 | +54 | 0.01 | Cont. |
| 33 | L-carnitine<br>Fish oil<br>Hexacosanol<br>Resveratrol<br>Coenzyme Q10 | 33.6 ± 3.2 | +46 | 0.05 | Cont. |
| 34 | L-carnitine<br>Monacolin K<br>Hexacosanol<br>Resveratrol<br>Coenzyme Q10 | 33.3 ± 3.3 | +45 | 0.05 | Cont. |
| 35 | L-carnitine<br>Monacolin K<br>Fish oil<br>Resveratrol<br>Coenzyme Q10 | 34.5 ± 3.1 | +50 | 0.01 | Cont. |
| 36 | L-carnitine<br>Monacolin K<br>Fish oil<br>Hexacosanol<br>Resveratrol<br>Coenzyme Q10<br>Vitamin B6<br>Vitamin B12<br>L-carnitine | 45.6 ± 4.6 | +83<br>+49<br>+39<br>+34<br>+36<br>+33<br>+34<br>+36<br>+36 | 0.001<br>0.01<br>0.05<br>0.05<br>0.05<br>0.05<br>0.05<br>0.05<br>0.05 | Cont.<br>15<br>21<br>22<br>25<br>26<br>27<br>28<br>31 |

The results reported above clearly demonstrate the unexpected synergism of the combination according to the present invention respect to the single elements or their minimal combinations.

In the following are reported some examples of the composition of the invention.

Composition 1

| (a) red rice extract | 200 mg |
|---|---|
| (b) fish oil | 600 mg |
| (c) L-carnitine tartrate | 147 mg |
| (d) policosanols (sugar cane extract) | 10 mg |
| (e) resveratrol | 10 mg |
| (f) Coenzyme Q10 | 10 mg |
| (g) vitamin B6 | 3 mg |
| (h) vitamin B12 | 2.5 µg (mcg). |

The invention claimed is:

1. Composition comprising (a) from 10 mg to 2000 mg of an extract of rice fermented with *Monascus purpureus*; (b) from 10 mg to 1000 mg of an omega-3 fatty acid; (c) from 10 mg to 1000 mg of L-carnitine or a salt thereof; (d) from 1 mg to 100 mg of a policosanol or a natural extract containing policosanols; (e) from 1 mg to 100 mg of resveratrol or a natural extract containing resveratrol; (f) from 1 mg to 100 mg of Coenzyme Q10;

for the treatment of hypertriglyceridemia or hypercholesterolemia.

2. The composition of claim 1, further comprising: (g) from 0.3 mg to 30 mg of vitamin B6 (h); and from 0.25 µg to 25 µg of vitamin B12.

3. A composition of claim 1 comprising: (a) extract of rice fermented with *Monascus purpureus* in a dose of 200 mg comprising 3 mg of Monacolin K; (b) fish oil in a dose of 600 mg comprising 120 mg of DHA and 165 mg of EPA; (c) L-carnitine tartrate in a dose of 147 mg corresponding to 100 mg of L-carnitine inner salt; (d) extract of sugar cane comprising policosanols in a dose of 10 mg; (e) resveratrol in a dose of 10 mg; (f) Coenzyme Q10 in a dose of 10 mg; (g) vitamin B6 in a dose of 3 mg; and (h) vitamin B12 in a dose of 2.5 µg.

4. The composition of claim 1, further comprising other vitamins, co-enzymes, mineral substances and antioxidants or active ingredients useful for treating lipid disorders.

5. The composition of claim 1, further comprising at least one pharmaceutically acceptable vehicle and/or excipient.

6. An orally administrable composition of claim 1, in liquid, semi-liquid or solid form; in sachets, pills, vials, ointment, gel, or liposome.

7. The composition of claim 1, wherein the salt of L-carnitine is selected from the group consisting of chloride, bromide, orotate, aspartate, acid aspartate, acid citrate, magnesium citrate, phosphate, acid phosphate, fumarate and acid fumarate, magnesium fumarate, lactate, maleate and acid maleate, oxalate, acid oxalate, pamoate, acid pamoate, sulphate, acid sulphate, glucose phosphate, tartrate and acid tartrate, glycerophosphate, mucate, magnesium tartrate, 2-amino-ethanesulphonate, magnesium 2-amino-ethanesulphonate, methanesulphonate, choline tartrate, trichloroacetate, and trifluoroacetate.

8. The composition of claim 1, wherein the policosanol is selected from the group consisting of triacontanol, hexacosanol, hexacontanol, ecocontanol, tetracosanol, dotriacontanol, and tetracontanol.

9. The composition of claim 1, wherein the policosanol is in the form of extract from natural products selected from the group consisting of: wheat germs, rice germs, sugar cane, or *Ginkgo biloba* leaves.

10. A composition of claim 1 comprising: (a) 200 mg of extract of rice fermented with *Monascus purpureus*; (b) 600 mg of an omega-3 fatty acid; (c) 100 mg of L-carnitine or a salt thereof as inner salt; (d) 10 mg of a policosanol or a natural extract containing policosanols; (e) 10 mg of resveratrol or a natural extract containing resveratrol; (f) 10 mg of Coenzyme Q10; (g) 3 mg of vitamin B6; and (h) 2.5 μg of vitamin B12.

11. Method of preventing or treating an altered lipid metabolism and complications thereof, in which said complications are selected from the group consisting of cardiovascular, atherosclerotic and/or thromboembolic diseases, which comprises administering to a patient in need thereof a suitable amount of the composition of claim 1.

* * * * *